United States Patent [19]

Manabe

[11] Patent Number: 4,540,549
[45] Date of Patent: Sep. 10, 1985

[54] CHEMICAL ANALYZING APPARATUS

[75] Inventor: Sugio Manabe, Kodaira, Japan

[73] Assignee: Olympus Optical Company Ltd., Japan

[21] Appl. No.: 684,170

[22] Filed: Dec. 21, 1984

Related U.S. Application Data

[63] Continuation of Ser. No. 359,934, Mar. 19, 1982, abandoned.

[30] Foreign Application Priority Data

Mar. 24, 1981 [JP] Japan .................. 56-41640

[51] Int. Cl.³ .................. G01N 21/13; G01N 21/77; G01N 35/04
[52] U.S. Cl. .................. 422/64; 422/67; 435/291; 435/808
[58] Field of Search .................. 422/63, 64, 65, 67; 435/291, 808

[56] References Cited

U.S. PATENT DOCUMENTS

| | | | |
|---|---|---|---|
| 4,265,544 | 5/1981 | Banno et al. | 435/291 X |
| 4,276,051 | 6/1981 | Ginsberg et al. | 422/67 X |
| 4,285,906 | 8/1981 | Meltzer et al. | 422/64 |
| 4,313,735 | 2/1982 | Yamashita et al. | 422/64 X |
| 4,315,891 | 2/1982 | Sakurada | 422/64 |
| 4,325,910 | 4/1982 | Jordan | 422/64 |

FOREIGN PATENT DOCUMENTS 0040189 3/1977 Japan .................. 422/64

Primary Examiner—Arnold Turk
Attorney, Agent, or Firm—Parkhurst & Oliff

[57] ABSTRACT

A turntable is arranged rotatably in both directions and a plurality of reaction vessels are arranged along a periphery of the turntable. Along the circumference of turntable are arranged a reagent delivery unit for delivering a given amount of reagent into successive reaction vessels, a sample delivery unit for delivering a given amount of samples into successive reaction vessels and a plurality of photometering units for measuring an absorbance of a test liquid contained in each reaction vessel. The turntable is first rotated in a backward direction by four steps and then is rotated in a forward direction by five steps, so that the turntable is advanced in the forward direction by one step at the end of the forward movement. Between successive backward and forward movements the test liquid is measured at a first time by the photometry unit and between successive forward and backward movements the same test liquid is measured at a second time by the same photometry unit and in this manner successive test liquids are measured twice by each of the photometry units. An analytical result can be obtained by processing all the measured values supplied from all the photometry units.

11 Claims, 2 Drawing Figures

CHEMICAL ANALYZING APPARATUS

This is a continuation of application Ser. No. 359,934 filed Mar. 19, 1982, now abandoned.

BACKGROUND OF THE INVENTION

The present invention relates generally to a chemical analyzing technique and, more particularly to a chemical analyzer comprising a plurality of photometering sections for monitoring a progress of reaction in a prompt and accurate manner in a rate assay.

For instance, measurement of an active value of enzyme in a serum sample is indispensable for clinical diagnosis and in hospitals a great number of serum samples have to be routinely tested. Since the active value of enzyme in the serum sample is usually very small, a very long time is required in order to measure the active value for each sample with high precision. Further, in order to obtain reliable data it is necessary to monitor or confirm a linear reaction, while the sample is maintained at a given constant temperature by means of a thermostat. It also takes a long time to effect such a confirmation. Nowadays the number of samples to be treated in hospitals or laboratories has increased and thus, it has become desirable to increase the number of samples which can be treated in a unit time, i.e. a treating ability.

In Japanese Patent Application Laid-open Publication No. 40,189/77 published on Mar. 28, 1977, there is proposed a chemical analyzer for measuring the activity value of enzyme wherein the analyzer has a high treating ability and can monitor the reaction progress for a relatively long time. In this known analyzer a number of reaction vessels are arranged with a given pitch P along a periphery of a turntable which can be rotated in the counterclockwise direction. A reagent delivery unit is provided at a reaction start point. Further, a single photometry unit is arranged at an upstream position with respect to the reaction start point when viewed in a counterclockwise rotational direction of the turntable. The photometry unit is separated from the reaction start point by such a distance that when the turntable is rotated in a counterclockwise direction by a distance of (n+1)P n+1 reaction vessels situated between the reaction start point and the photometry unit and containing samples have passed through the photometry section. After one cycle of the counterclockwise, the turntable has been advanced by one pitch in the forward direction so that each sample in the reaction vessels is measured.

However, in the above mentioned known analyzer since only one photometry unit is provided, it is impossible to increase the measurement accuracy and monitoring time period without sacrificing the treating ability. That is to say, when the monitoring time is to be prolonged, the distance between the reaction start point and the photometry position must be long so as to pass a greater number of reaction vessels through the photometry section. This results in lengthening the time required for the turntable to advance by one pitch and thus, the treating ability is decreased. Contrary to this, when the treating ability is improved by decreasing the period of one pitch advance, the monitoring time is shortened.

SUMMARY OF THE INVENTION

The present invention has as its object to provide a novel and useful chemical analyzer which can solve the aforementioned conflicting problems of the known analyzer by providing a plurality of photometry units along a reaction line so that the analyzer can have a long monitoring time period as well as a high treating ability. The plurality of photometry units are preferably arranged equidistant from one another along the reaction line.

It is another object of the present invention to provide a chemical analyzer which can produce accurate measuring results even if the characteristics of a plurality of equidistantly arranged photometry units are not exactly identical with each other.

According to the present invention, the chemical analyzer comprises
  means for defining a reaction line;
  means for transporting a plurality of reaction vessels along said reaction line successively in backward and forward directions repeatedly to advance the reaction vessels in the forward direction step by step; p1 means for delivering samples and at least one reagent into successive reaction vessels to form in each reaction vessel, a test liquid which is a mixture of a sample and at least one reagent;
  means including a plurality of measuring units arranged along the reaction line, each of which measuring unit measures each test liquid twice to produce measured values when a reaction vessel containing the relevant test liquid is stopped at the relevant measuring unit between successive backward and forward movements and between successive forward and backward movements of the reaction vessels along the reaction line; and
  means for receiving the measured values supplied from the measuring units to derive analytic results.

DESCRIPTION OF THE PREFERRED EMBODIMENTS

Figure 1:
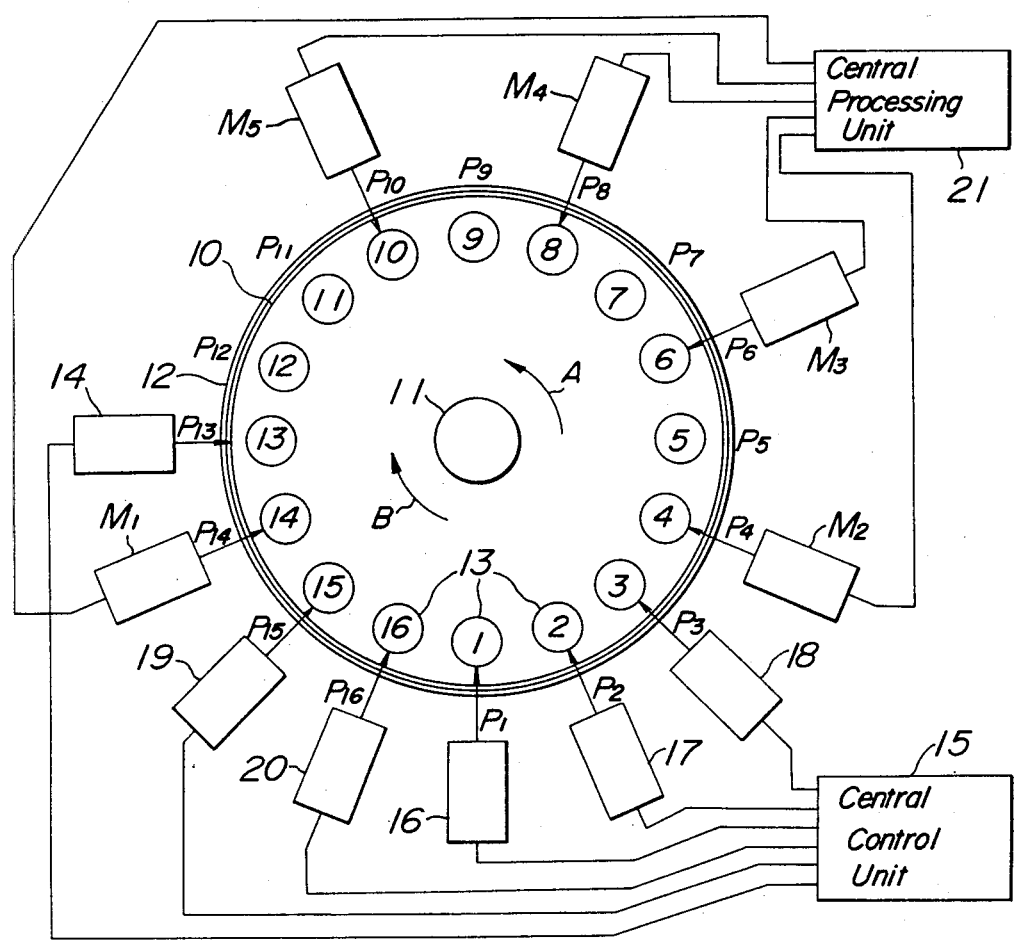
FIG. 1 is a schematic view showing an embodiment of the chemical analyzer according to the present invention.

FIG. 1 is a schematic view showing an embodiment of the chemical analyzer according to the present invention. The analyzer comprises a turntable 10 which is rotatably supported about a shaft 11. Below the turntable 10 is arranged a thermostat 12. In the drawing only a periphery of the thermostat is seen. The turntable has formed therein along its periphery a number of holes 13 for removably supporting reaction vessels to constitute a circular reaction line. For the sake of simplicity, the holes 13 are denoted by circles including digits 1 to 16 therein and in the following explanation the reaction vessels are also represented by the same digits. For instance, a reaction vessel fit in the hole 13 denoted by a digit 2 is also represented as a reaction vessel 2. The turntable 10 is rotated by a turntable driving mechanism 14 which is controlled by a central control unit 15. The driving mechanism 14 may comprise a motor, a gear connected to an output shaft of the motor and a gear secured to the turntable concentrically therewith and engaged with said gear. Further the reaction vessel holding holes 13 may be recesses and the reaction vessels may be held in position by frictional engagement of the vessels and recesses.

Along the circumference of the turntable 10 there are arranged various units. At a position $P_1$ there is arranged a reaction vessel loading unit 16 which can automatically supply clean reaction vessels into successive reaction vessel holding holes 13. At a next position $P_2$ is arranged a reagent delivery unit 17 for delivering a given amount of a given reagent into successive reaction vessels. At a position $P_3$, there is provided a sample delivery unit 18 for delivering a given amount of samples into successive reaction vessels. Therefore, the position $P_3$ may be considered as a reaction start point. According to the present invention, a plurality of, i.e. five photometry units $M_1$, $M_2$, $M_3$, $M_4$ and $M_5$ are arranged at positions $P_{14}$, $P_4$, $P_6$, $P_8$ and $P_{10}$, respectively. At position $P_{15}$ there is provided a unit 19 for mixing or stirring samples and reagent in the reaction vessels, and at a position $P_{16}$ is arranged a unit 20 for automatically removing the used reaction vessels from the turntable 10. As the reagent and sample delivery units 17 and 18 use may be made of any known liquid delivering device which can deliver a predetermined small amount of liquid into the reaction vessels without causing serious contamination. Further, the stirring unit 19 may comprise any known stirring mechanism which can fully agitate the liquid in the reaction vessels without causing contamination between successive samples. The reaction vessel removing unit 20 may be constructed of a known automatic unloader. The reaction vessel supplying unit 16, the reagent and sample delivery units 17 and 18, the stirring unit 19 and the reaction vessel removing unit 20 are all connected to the central control unit 15 and are controlled thereby as will be explained hereinbelow. Output signals generated by the five photometry units $M_1$ to $M_5$ are supplied to a central processing unit 21 in order to derive measurement results.

Figure 2:
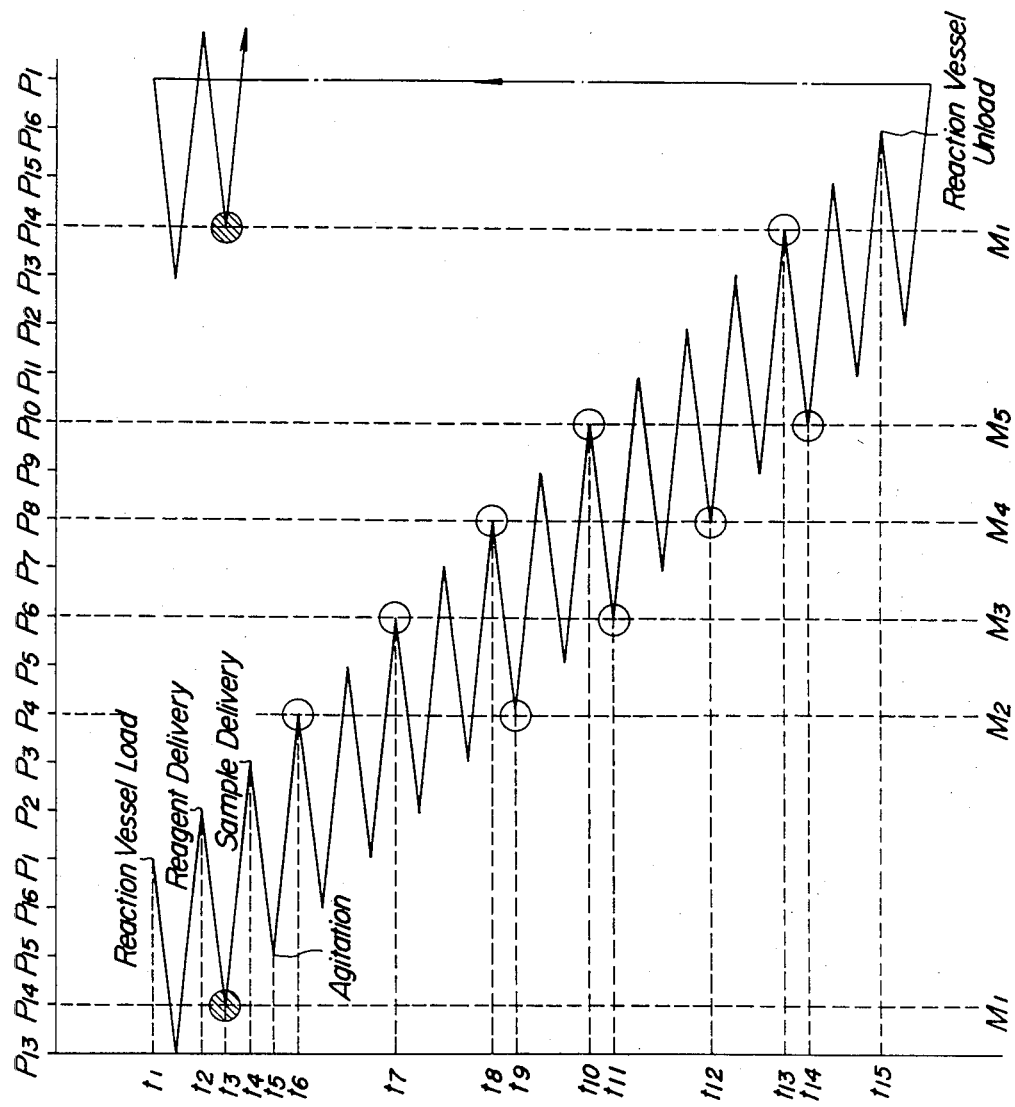
FIG. 2 is a chart for explaining an operation of the chemical analyzer illustrated in FIG. 1.

The operation of the chemical analyzer shown in FIG. 1 will be now explained with reference to a chart illustrated in FIG. 2. In this chart the vertical axis represents time and a horizontal axis denotes the position on the reaction line. That is to say, the chart shows a locus of movement of a reaction vessel 1 initially situated at the position $P_1$. The reaction vessel 1 is supplied from the unit 16 into the hole 13 of the turntable 10 at a time $t_1$. Then the turntable 10 is rotated in a backward direction shown by arrow B in FIG. 1 by four steps and is stopped. Then the reaction vessel 1 is indexed at the position $P_{13}$. Next the turntable 10 is rotated in a forward direction illustrated by arrow A by five steps and the reaction vessel 1 comes into the position $P_2$. In this manner, the turntable 10 is advanced by one step. It should be noted that the turntable 10 may be rotated in an intermittent manner or in a continuous manner, but the continuous movement can offer a higher treating ability. It is matter of course that one step is equal to a distance between adjacent reaction vessel holding holes 13.

While the reaction vessel 1 is stopped at the position $P_2$, a given amount of a given reagent specific to an item to be tested is delivered into the reaction vessel 1 at a time $t_2$ by means of the reagent delivery unit 17. Now the turntable 10 is rotated in the backward direction B by four steps and the reaction vessel 1 is stopped at the photometry unit $M_1$ at the position $P_{14}$. At a time $t_3$ a light beam having a given wavelength specific to the reagent is projected upon the reaction vessel 1 containing the reagent to measure the optical property, e.g. light absorbance representing modification or alteration of the reagent and a blank value of the reaction vessel 1. For this purpose, the reaction vessels must be made of material transparent to the light beam. An output signal derived by the photometry unit $M_1$ is supplied to the central processing unit 21 and processed and stored therein.

Next the turntable 10 is advanced by five steps in the direction A and the reaction vessel 1 is stopped at the position $P_3$ at which the delivery unit 18 supplies a given amount of a sample into the reaction vessel 1 at a time $t_4$. After that the turntable 10 rotates in the reverse direction B by four steps and the reaction vessel 1 is indexed at the position $P_{15}$ at which a test liquid which is a mixture of the reagent and sample is agitated by the stirring unit 19 at a time $t_5$. The reaction vessels are disposed in the thermostat 12 and the test liquids in the reaction vessels are maintained at a given constant temperature to proceed the reaction. Next the turntable 10 is advanced by five steps and the reaction vessel 1 is stopped at the position $P_4$ at which the photometry unit $M_2$ is provided. The optical property of the test liquid in the reaction vessel 1 is measured by the photometry unit $M_2$ at a time $t_6$ to derive a first measured value which is supplied to the central processing unit 21 and is stored therein. In this manner the test liquid in the reaction vessel 1 is measured by the photometry unit $M_3$, $M_4$ and $M_5$ at time $t_7$, $t_8$ and $t_{10}$, respectively not only at the end of the forward movement, but also at the end of the backward movement at time $t_9$, $t_{11}$, $t_{12}$ and $t_{14}$, respectively. Therefore, now considering only the photometry unit $M_2$, the liquid is measured twice, once at the end of the backward movement and once at the end of the forward movement. By deriving a difference between the measured values obtained by said two measurements, it is possible to produce an amount of variation of the optical property with respect to time ($t_9 - t_6$). Similar differences can be derived from the values obtained by the other photometry units $M_3$, $M_4$ and $M_5$. In case of measuring the active value of enzyme by the kinetic assay method, these differences are compared with each other to confirm a linearity of reaction and thus, a very accurate measuring result can be obtained. The photometered data derived by the photometry unit $M_1$ at time $t_3$ can be used to correct the measurement result. When the reaction vessel 1 is stopped at the position $P_{16}$, the reaction vessel 1 is removed from the turntable 10 by means of the unit 20 at a time $t_{15}$.

In an end point method the measurement result can be obtained by deriving a difference between the first value measured by the photometry unit $M_1$ at time $t_3$ and a second value measured by the same photometry unit $M_1$ at time $t_{13}$. Similar measurement may be effected in one point method in case that the reaction has not been finished by time $t_{14}$.

It should be noted that in the above explanation only the single reaction vessel 1 is considered, but the above process is simultaneously effected for all the reaction vessels. For instance, at time $t_1$, the following steps are carried out.

(a) a sample is delivered into a reaction vessel 2;
(b) a reagent is delivered into a reaction vessel 3;
(c) test liquids in reaction vessels 4, 6, 8 and 10 are measured by the photometry units $M_2$, $M_3$, $M_4$ and $M_5$, respectively;
(d) a reagent in a reaction vessel 14 is measured by the photometry unit $M_1$;
(e) sample and reagent in a reaction vessel 15 is agitated by the stirring unit 19; and (f) a used reaction vessel 16 is removed from the turntable 10 by the automatic unloader 20.

In case of measuring Glumatate Oxalacetate Transaminase (GOT) with a reagent amount of 1.0 ml and a sample amount of 100 μl, a median value of 20 units for a normal sample shows an absorbance variation of about 0.011 for a minute. In a known analyzer in which an absorbance variation is derived from values measured by different photometry units, even if the linearities of the photometry units differ from each other only by 0.1%, an error of 0.002 in the absorbance value might be produced near the absorbance of 2. Contrary to this, in the analyzer according to the invention since the error of 0.1% is produced only for the median value of 20 units, the error introduced in the measurement will be decreased to only 0.011×(1/1000.) Therefore, according to the present invention, the variation between the photometry units can hardly affect the accuracy and precision of the measurement.

In the above embodiment one cycle is composed of the backward rotation of four steps, stop, first photometering, forward rotation of five steps, stop and a second photometering. It is now assumed that this one cycle operation is carried out within ten seconds, then it is possible to measure the progress of reaction over a very long time of forty five seconds. Contrary to this, in a known analyzer in which the reaction vessels are fed only in the forward direction in a stepwise manner, if it is assumed that the reaction vessels are advanced by one step for ten seconds, the progress of reaction can be monitored only over a short time of twenty seconds. Moreover according to the invention, it takes a rather long time period of about 115 seconds for the reaction vessel advancing from the reaction start point $P_3$ to the position $P_{10}$ of the last photometering unit $M_5$ and thus, the measuring precision can be increased to a great extent. Contrary to this in the known analyzer, the measurement at the last photometry unit is effected about 70 seconds after the reaction start point.

As apparent from the above description, according to the present invention the measurement is effected at each photometry unit at least twice during the substantially reciprocal movement of the turntable and thus, the measurement time interval can be prolonged to increase the measurement precision and at the same time the treating ability can be increased. Further the concentration or the activity value of enzyme can be derived from the values measured by the same photometry unit and thus, precise and accurate measurement results can be attained even if a plurality of the photometry units do not have the same properties.

It should be noted that the present invention is not limited to the embodiment explained above, but various modifications and changes are conceived within the scope of the invention. For instance, in the above embodiment the reaction vessels are of a disposable type, but they may be of a repeatedly usable type. In such a case, the test liquids in the reaction vessels may be discharged at the position $P_{16}$ and the reaction vessels may be washed and dried at the position $P_1$. The drying operation is advantageously effected only when the relevant reaction vessel is to be filled with reagent and sample and if reagent and sample are not delivered in the relevant reaction vessel, it will be preferable that the relevent reaction vessel is remained to be filled with a washing liquid so as to prevent the reaction vessel from being contaminated. Further it is not always necessary to arrange the photometry units equidistantly along the circumference of the turntable, i.e. the reaction line. For instance, if it is required to monitor a first portion of the progress of reaction more in detail, the photometry units may be arranged much closer to each other in a first portion of the reaction line than in the remaining portion of the reaction line. Moreover, the numbers of steps of each forward and backward movements of the reaction vessel array may be set to different numbers from those in the above embodiment as long as each test liquid can be measured twice at respective photometry positions. Further, more than one reagent delivery unit may be arranged. In case of effecting a single line-multi item test by means of the analyzing apparatus according to the present invention, the photometry units may select a light beam of a particular wavelength in accordance with a test item. This may be done simply by selectively inserting a filter in the optical path.

Moreover, in the above embodiment the reaction vessels are arranged along the periphery of the turntable so as to make the reaction line circular, but the reaction vessel transporting device may be constituted by any other means such as an endless chain and an endless belt. In such a case the reaction line may be formed as any desired configuration such as oval and elliptic. Further the reaction line is not always necessary to be endless, but a linear reaction line may also be used.

What is claimed is:

1. A chemical analyzer comprising
   means including a turntable for defining a circular reaction line and transporting a plurality of reaction vessels along said circular reaction line;
   means for rotating said turntable in a backward direction by n pitches and in a forward direction by n+1 pitches repeatedly to advance said reaction vessels in the forward direction step by step;
   means for delivering a sample and at least one reagent into successive reaction vessels to form in each reaction vessel a test liquid which is a mixture of said sample and said at least one reagent;
   means including a plurality of measuring units arranged along said circular reaction line, each of said measuring units measuring each test liquid twice to produce two measured values when a reaction vessel containing a relevant test liquid is stopped at a relevant measuring unit between successive backward and forward movements and between successive forward and backward movements of said reaction vessels along said circular reaction line; and
   means for receiving two measured values for a test liquid supplied from each of said measuring units to derive a difference between said two measured values supplied from each of said measuring units to derive analytic results for each test liquid.

2. The chemical analyzer of of claim 1, wherein at least one of said plurality of measuring units is arranged at an upstream position with respect to said delivering means.

3. The chemical analyzer of claim 1, wherein said delivering means comprises a reagent delivering unit for delivering an amount of a reagent into successive reaction vessels, and a sample delivery unit for delivering an amount of successive samples into successive reaction vessels.

4. The chemical analyzer of claim 3, wherein said reagent delivering unit is arranged at an upstream position with respect to said sample delivering unit.

5. The chemical analyzer of claim 4, wherein one of said plurality of measuring units is arranged at an upstream position with respect to said reagent delivery unit, and the reaction vessel into which only the reagent has been delivered is measured by said one of the measuring units.

6. The chemical analyzer of claim 1, wherein said plurality of measuring units are arranged equidistantly along said reaction line.

7. The chemical analyzer of claim 1, further comprising means for agitating a test liquid in a reaction vessel before said reaction vessel is stopped at the measuring units.

8. The chemical analyzer of claim 1, wherein said turntable is capable of holding said reaction vessels along its periphery.

9. The chemical analyzer of claim 8, wherein said turntable comprises a plurality of portions formed along its periphery for holding said reaction vessels.

10. The chemical analyzer of claim 9, further comprising means for automatically supplying new reaction vessels into successive holding portions of said turntable, and means for automatically removing used reaction vessels from said holding portions.

11. The chemical analyzer of claim 1, wherein each of said plurality of measuring units comprises a photometering unit for measuring an absorbance of the test liquid.

* * * * *